United States Patent
Neuberger

(10) Patent No.: US 8,257,347 B2
(45) Date of Patent: Sep. 4, 2012

(54) VEIN TREATMENT DEVICE AND METHOD

(75) Inventor: Wolfgang Neuberger, F.T. Labuan (MY)

(73) Assignee: Biolitec Pharma Marketing Ltd., F.T. Labuan (MY)

( * ) Notice: Subject to any disclaimer, the term of this patent is extended or adjusted under 35 U.S.C. 154(b) by 1300 days.

(21) Appl. No.: 11/900,248

(22) Filed: Sep. 11, 2007

(65) Prior Publication Data

US 2008/0065058 A1    Mar. 13, 2008

Related U.S. Application Data

(60) Provisional application No. 60/843,875, filed on Sep. 12, 2006.

(51) Int. Cl.
*A61B 18/22* (2006.01)

(52) U.S. Cl. .............. 606/15; 128/898; 606/3; 606/9

(58) Field of Classification Search .............. 128/898; 606/2–19
See application file for complete search history.

(56) References Cited

U.S. PATENT DOCUMENTS

| | | | |
|---|---|---|---|
| 5,531,739 A | 7/1996 | Trelles | |
| 5,578,029 A | 11/1996 | Trelles et al. | |
| 6,398,777 B1 | 6/2002 | Navarro et al. | |
| 6,964,661 B2 * | 11/2005 | Rioux et al. | 606/41 |
| 6,986,766 B2 * | 1/2006 | Caldera et al. | 606/15 |
| 7,524,316 B2 * | 4/2009 | Hennings et al. | 606/7 |
| 2002/0002367 A1 * | 1/2002 | Tankovich et al. | 606/3 |
| 2004/0092913 A1 | 5/2004 | Hennings et al. | |
| 2005/0015123 A1 * | 1/2005 | Paithankar | 607/88 |
| 2005/0131400 A1 * | 6/2005 | Hennings et al. | 606/15 |
| 2005/0203497 A1 * | 9/2005 | Speeg et al. | 606/15 |
| 2006/0161142 A1 * | 7/2006 | Sierra et al. | 606/9 |
| 2006/0217692 A1 * | 9/2006 | Neuberger | 606/12 |

OTHER PUBLICATIONS

"The combination of optical and electrical energies produces different histological findings from when laser alone is used in leg vein treatment", Trelles, Mario A, Lasers in Medical Science, vol. 19, No. 3, 165-166, DOI: 10.1007/s10103-004-0318-6 Nov. 2004.*

* cited by examiner

*Primary Examiner* — Henry M Johnson, III
(74) *Attorney, Agent, or Firm* — Bolesh J. Skutnik; BJ Associates

(57) ABSTRACT

Device/system and treatment method of varicose veins and other vein abnormalities are presented. Treatment A comprises combining two wavelengths to occlude abnormal veins. Wavelengths are chosen as effective absorption peaks of hemoglobin and/or water, e.g. 980 nm and 1460 nm. Irradiations of blood, collagen and water in the vessel cause occlusion/shrinkage. Constant power-density is used based on fiber withdrawal speed and structural vein parameters. Treatments employ dual laser wavelengths or highly-controlled vein-wall damage wavelengths. Monitored control parameters and predetermined vein structural parameters. Alternatively, 1460+60 nm laser energy is employed, having high absorption in the vein wall, creating little thermal stress outside the vein, and being effective in initiating damage reaction response. Treating at 1460+60 nm has benefits of high vein closure rates and favorable post-operative results, i.e., little post-operative pain/discomfort, brusing/inflammatory reactions, due to their very high absorption in small volumes of the collagen/water in vein walls.

13 Claims, 4 Drawing Sheets

VEIN TREATMENT DEVICE AND METHOD

DOMESTIC PRIORITY UNDER 35 USC 119(e)

This application claims the benefit of U.S. Provisional Application Ser. No. 60/843,875 filed Sep. 12, 2006, entitled "Vein Treatment Device and Method" by Wolfgang Neuberger, which is incorporated by reference herein.

BACKGROUND OF THE INVENTION

1. Field of the Invention

The invention is a device/system and method for the percutaneous treatment of veins. In particular, the device and method are directed at the destruction of veins by endovenously irradiating abnormal or diseased veins with wavelengths at about 980 nm and about 1460 nm, in combination, or with the latter alone, to affect destruction of the vein.

2. Invention Disclosure Statement

The present invention is a device and method for endovenous thermal treatment of diseased or abnormal veins; especially varicose veins. An increasing number of individuals are seeking treatment of lower extremity veins for symptomatic, as well as cosmetic concerns. The use of endovascular treatment enables proximal access to a vascular treatment site enabling use of a less harmful and less powerful laser, when compared to surface treatment lasers which are more powerful and cause damage to surrounding tissue and are not an effective treatment.

Veins are thin walled vessels containing many one way valves which open to allow the blood to flow in one direction and close to prevent back flow. These valves might grow weak or malfunction which increases the blood volume in the vessels causing the vessel walls to dilate or enlarge due to the pressure exerted on the walls. Varicose veins is a common medical condition among adults with symptoms such as swelling, aching, itching and discomfort in the legs with cosmetic deformities visible in many cases. If left untreated varicose veins can cause many medical complications.

The use of lasers in the treatment of various vascular diseases, such as facial telangiectasias and some lower extremity veins externally has been achieved with some success. In this technique laser energy is irradiated on the surface of the skin which on penetration is absorbed by the blood which coagulates and collapses the blood vessel. Larger varicose veins located in deeper soft tissue cannot be treated with this method as higher powers are required. This could also lead to side effects including scarring and skin pigmentation changes.

Various forms of treatment are present, for temporary relief such as the use of compression stockings or elevating the effected area is common. Common long term treatments for varicose veins include sclerotherapy, ambulatory phlebectomy, ligation and stripping of the greater saphenous vein in cases of sapheno-femoral junction incompetence. Sclerotherapy involves introduction of a chemical irritant into the vein. The chemical acts on the vein walls causing the walls to occlude and block the blood flow. Complications can be severe causing skin ulceration, skin reactions and permanent staining. Treatment is also limited to certain vein size ranges and there is relatively high recurrence rate due to vessel recanalization. Surgical excision requires the use of anesthetic and involves long recovery periods. Even though it has a high success rate it is an expensive process and complications from surgery can arise. Surgical excision also leaves behind permanent scarring and deformities on treated areas.

Ambulatory phlebectomy involves use of multiple incisions through the skin along the length of the vein to remove the vein. The process is relatively lengthy, expensive and leaves behind visible scars on the tissue.

One other technique used to treat varicose veins is RF energy which delivers electrical heat directly to the vessel wall; this technique has a more uniform application of energy along the vessel walls. But the catheters used are expensive and complicated; also the catheter heats up inside the vein and indiscriminately causes surrounding tissue damage in many cases. Because diode lasers use a small fiber and because the heat remains inside the vessel, smaller vessels on the surface of skin can be treated. This cannot be done using the radio frequency technique.

Endovascular laser therapy is a relatively new technique for venous reflux disease. In this technique an optical fiber is percutaneously inserted into the vein to be treated. Laser energy is then radiated through the bare fiber tip into the vessel. The energy contacts the contents of the vein causing the vein to occlude or collapse. The laser is slowly withdrawn along the entire segment of the vein to be treated.

Prior techniques to treat varicose veins have attempted to heat the vessel wall by targeting the hemoglobin in the blood and then having the heat transfer to the wall. The wavelength ranges from 500 nm to 1100 nm and scatters in tissue compared to other wavelengths. These wavelengths penetrate to varied depths unless stopped by an absorbing media. The wavelength ranges from 500 nm to 1100 nm could cause damage to surrounding tissue if the power levels are not within safe limits. The blood in veins absorbs these wavelength energies in less than 1 mm in the presence of hemoglobin. This causes blood to heat up quickly and damage the vein wall by conduction and not by direct wall absorption. These wavelength ranges are however good for the absorption of blood as seen by the absorption peaks of Hemoglobin and Oxy-hemoglobin around the 980 nm wavelength, but will not occlude the vein walls by conduction of this heat from the blood to the vein walls as this requires use of higher powers and longer pulse durations at a particular site. The higher wavelengths have a much higher water and collagen absorption in vein walls as seen in absorption peaks around the 1460 nm wavelength.

In Publication U.S. 2004/0092913 by Hennings et al., a device and method are given for the treatment of varicose veins or the greater saphenous vein. The device includes a laser of 1320 nm wavelength used for treatment to occlude and reabsorb the vein. The fiber optic catheter may have a frosted or diffusing tip catheter, a motorized pull back device and thermal sensor to track temperature in vessel. This technique requires drainage of blood before lasing to effectively occlude the vein walls. The energy absorbed by blood in this wavelength range is relatively low hence effective absorption of blood in this range is not observed. This could lead to improper or incomplete treatment in the treated vein if blood is present. Also the use of cooling mechanism is seen which indicates use of higher energy to provide a means to minimize surrounding tissue damage. The use of higher energies or longer durations of exposure at a site results in damage to peripheral veins and surrounding tissue.

In U.S. Pat. No. 6,398,777 by Navarro et al., describes use of laser energy wavelengths from about 532 nm to about 1064 nm for treating blood vessels. This technique requires application of pressure over the laser tip and emptying of the vessel of blood to ensure contact between the vessel wall and fiber tip at the start and throughout the treatment. This necessity can result in vessel perforation and force blood into surrounding tissue or veins causing discomfort and bruising. The laser energy directed at the contact point causes perforations in the wall and surrounding area, directly or indirectly These wavelength ranges require a cooling mechanism to minimize burning caused by transmitted energy.

In U.S. Pat. No. 5,531,739 by Trellas and U.S. Pat. No. 5,578,029 by Trellas et al., a device to perform under skin laser treatment is described. The treatment is limited to depths that are specifically used for different treatments. The treatment necessitates multiple insertions along the length of treatment vein for effective occlusion along the length. The technique is cumbersome and expensive as specialized tips are needed. The laser energy is delivered to the vicinity of the vein which causes closure of the vein by collapsing its wall which is an indirect solution. By the introduction of multiple punctures in the skin the risk of infection is increased. The use of near vein radiation also might cause disfiguration of the skin surface and damage to surrounding tissue. Since treatment is near a vein the radiation is also applied to nerves which can be painful to the patient.

In prior art, usage of 10 to about 20 W is required because the laser wavelengths are not effectively coupled to the vessel walls, are absorbed by the blood or are transmitted through the vessel walls. In such cases external cooling devices are necessary to prevent burns on the skin surface. In some cases the fiber tips need to be conditioned in order to provide satisfactory results because of the way these laser wavelengths interact with water and tissue. By trapping heat in the fiber tip, the "hot tip" can reach temperature exceeding 400° C. Also the energy from these lasers is absorbed by the conditioned tips and not in water, hemoglobin or tissue. Conductive heat transfer can damage collateral tissue causing swelling, tissue necrosis, charring and patient discomfort.

A need exists for an endovascular percutaneous laser treatment device/system and method for the treatment of varicose veins with capability for the surgeon or operator to select an optimum combination of wavelengths for absorption in hemoglobin and water in order to produce direct endothelial and vein wall damage with subsequent fibrosis, without incurring the problems and deleterious side effects associated with the prior art.

OBJECTIVES AND BRIEF SUMMARY OF THE INVENTION

It is an objective of the present invention to provide a device/system and method for varicose vein treatment with the capability for the operator to select different wavelength combinations of about 980 nm and about 1460 nm. Also a treatment power range is to be considered in order to get an optimum combination for absorption of water, collagen and hemoglobin present in the veins.

It is a further objective of the present invention to address the need for an effective percutaneous endovascular laser treatment which utilizes a control mechanism that delivers the predetermined energy to the vein based on manual pull back speed of the fiber in the vein and a vein's physical parameters.

It is another objective of the present invention to provide a device/system and method to improve the accuracy of underskin treatments. This is provided by feedback from a control mechanism to the user in order to choose suitable power, pull back distances and speeds based on available vein parameters to induce effective treatment.

It is still another objective of the present invention to provide a motorized pull back mechanism connected to the control mechanism, which further aids in providing a controlled ideal treatment method for abnormal veins.

It is still a further objective of the present invention to use a fused quartz diffuser tip on the fiber end, to enhance radiation delivery from the fiber tip to the vessel wall.

Briefly stated, the present invention provides a device/system and a method for the treatment of varicose veins and other varices or vein abnormalities. In one preferred embodiment, the treatment comprises a combination of two wavelengths to effectively occlude abnormal veins. The wavelengths are chosen as the effective absorption peaks of hemoglobin and water, which are seen at these wavelengths, approximately 980 nm and 1460 nm respectively. The vein is targeted with these wavelengths to obtain maximum and effective absorption. The Near Infra Red laser radiations are delivered to blood, collagen and water in the vessel which results in occlusion and shrinkage of the vein. In this technique an optical fiber is inserted into the vein and laser sources are used to irradiate the vein. A control mechanism allows delivery of constant power density based on feedback about speed of fiber withdrawal and local structural vein parameters. This technique is an effective treatment for vein disorders as the treated vein is targeted with dual wavelengths of energy or alternatively with a wavelength having highly controlled vein-wall damage character. The treatment conditions are based on feedback from different control parameters that are monitored and preliminary predetermined structural parameters of the treatment site. The device involves a side firing optical fiber which can also irradiate nearly uniform circumferentially from said fiber's distal end. Alternatively, in another preferred embodiment 1460±60 nm laser energy is employed, which with its high absorption in the vein wall, creates little thermal stress outside the vein, and is very effective in initiating the damage reaction response, shrinkage in the vein wall. An example is using, e.g., a 1470±20 nm wavelength. Laser vein treatments administered using 1460±60 nm have the benefits of high vein closure rates and extremely favorable post-operative results, i.e., little, if any, post-operative pain/discomfort, brusing or inflammatory reactions, due to their very high absorption in small volumes of the collagen/water in vein walls.

The above and other objects, features and advantages of the present invention will become apparent from the following description read in conjunction with the accompanying drawings, in which like reference numbers in different drawings denote like items.

DETAILED DESCRIPTION OF PREFERRED EMBODIMENTS

Figure 1:
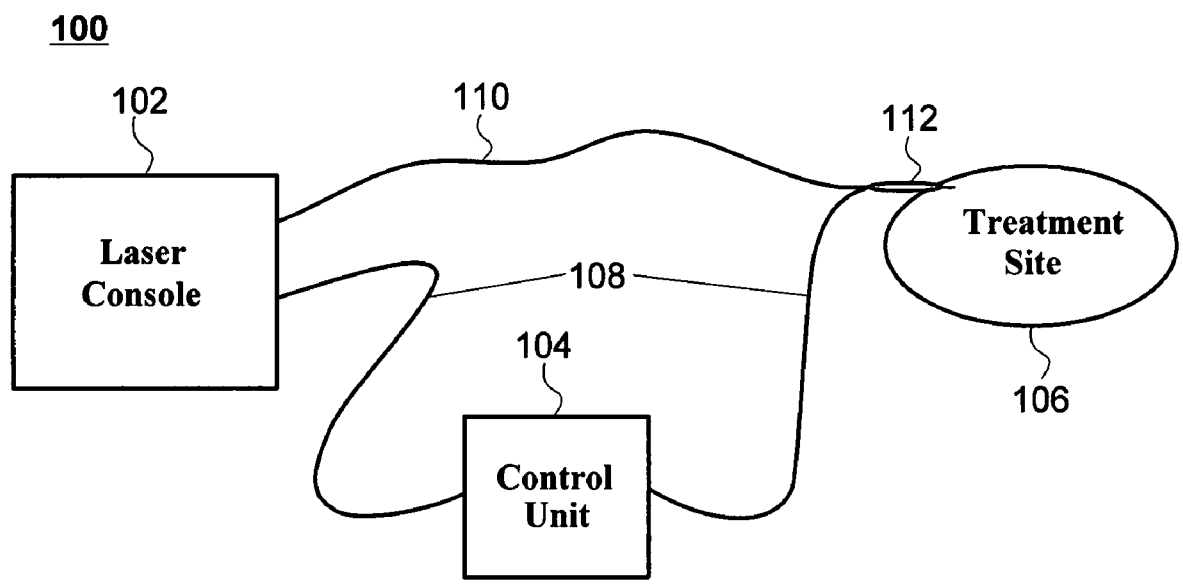
FIG. 1 illustrates a representative schematic diagram of the apparatus for performing varicose vein closure procedure.

The present invention describes a device/system and method for the treatment of many vein abnormalities; especially varicose veins. The method is useful for under-skin laser treatments of skin irregularities, vascular abnormalities and general assistance in surgical procedures. The device/ system and method essentially applies to all body structures that can be affected by laser treatment including superficial, subcutaneous structures, as well as internal organs and tissues. The variable use to which the present invention could be put to use makes it a beneficial, efficient and practical for under skin laser treatment system for practitioners to use. Different wavelengths of lasers are used to treat abnormal tissue with predetermined energy. This technique allows less energy to be used to effectively occlude the vein and helps prevent damage to surrounding tissue and perforation in vessel walls.

The near infra red region of 1.2 nm to 1.8 nm is useful to heat and shrink collagen in the walls. Trials have shown that use of this energy range does not result in perforation of the vessel wall even if the fiber remains in one location for several seconds. Experiments have shown that use of this range of energy results in little pain or collateral bruising as the vessel wall always stops the energy.

The invention describes a device/system and method that delivers two wavelengths, one about 980 nm and another of about 1460 nm of laser energy with a range of power options to select from to treat varicose veins or abnormal tissue. It also describes a device and method delivering only about 1460 nm laser energy with a range of power options to select from to treat varicose veins or abnormal tissue. In such procedures it is important to deliver a clinically effective dose of energy to tissue without unnecessary damage to surrounding tissue. The present invention also ensures that the required power is delivered regardless of the practitioner and thus avoids human error.

Endovascular delivery of laser energy in the form of dual wavelength combinations or a single wavelength in the range of near-IR to abnormal veins in order to effectively occlude them without causing any side effects is key in the present invention. This decreases the power necessary to treat the vein and eliminate the possibility of side effects to overlying skin and surrounding tissue. In addition fibrosis of the vessel is preferred because veins of varying diameters can be effectively treated. Users may therefore apply treatment with the present invention on superficial and deep lying veins, as well as internal organs and tissues.

In the first step an insertion is made through a catheter or needle with or without a hand-piece to introduce the optical fiber through an access vein to the treatment site. An imaging technique such as X-ray imaging or ultrasound is utilized to move the fiber to a position near the sapheno-femoral junction in case of varicose veins or distal end of treatment site. Additional visualization techniques are used to pin point the position of the fiber tip or output tip in the vein. The fiber tip that delivers the radiation to the vein is initially positioned at the distal end of treatment site prior to administration of laser radiation.

In the case of the combination of wavelengths, a few flashes in the pulsed mode are administered at 980±20 nm to occlude and seal the vein at the distal end of vein. Now laser delivery is changed to continuous mode for the remaining length of the treatment vein. The hand piece has a reference measure to monitor the exact distance of the fiber that is present in the vein. This is accomplished as the optical fiber has markings on them which give a reference as to the depth of fiber present in vein. Laser energy with dual wavelengths of 980±20 nm and 1460±60 nm is next administered to the vein in different combinations as required for effective treatment. The possible radiation combinations are: (a) first the 980 nm is delivered followed by the 1460 nm, (b) first the 1460 nm is delivered followed by the 980 nm, (c) both the wavelengths can be simultaneously delivered to a treatment site, or (d) the wavelengths can be individually delivered to a treatment site; all depending on the need of the patient. The 980 nm is useful for absorption in blood-hemoglobin and water. The 1460 nm is useful for high absorption in water and collagen absorption in the vein walls while having much lower absorption in hemoglobin. The radiation combinations are chosen for specific treatment sites and for preset power ranges and operation modes including pulse, continuous, etc. Radiation protocols are selected based on the feedback from parameters obtained from the control unit prior to and also during treatment. The radiation combination or individual radiation wavelength is chosen followed by power range selection. After selecting the parameters, treatment is administered to the site.

Additionally we have found that using the 1460±60 nm alone can also lead to painless, effective closure of veins, since its absorption by the water/collagen in the vein wall is very strong and within a fraction of typical wall thickness. This provides like in the combination case a safe closure at greater efficiency and less patient pain than normal wavelengths and substantially equivalent to the combination approach.

Following irradiation the fiber is withdrawn at a pre-determined rate till the fiber tip reaches the proximal part of the abnormal vein section. The irradiation from a fiber tip is emitted in a uniform manner onto the treatment tissue. Additionally for better energy delivery to treatment tissue in certain cases, the fiber tip could be a side-firing tip. Based on the feedback on fiber withdrawal speed which is monitored relatively by the hand-piece, the control unit monitors the energy delivered to the vein. The predetermined vein dimensions and vein content parameters are also monitored by the control unit to deliver energy to the treatment site. This inbuilt feature of the system enables minimal intervention and minimum human errors.

The features presented in the figures below generally apply to either the combination of 980±20 nm+1460±60 nm irradiations or to the sole 1460±60 nm irradiations, except where specific reference to each wavelength is described.

FIG. 1 is a representation of the basic schematic block diagram 100 of the apparatus to be used for performing varicose vein closure. The system consists of laser console 102, control unit 104 and treatment site 106. Control unit 104 gathers information about the different parameters of treatment site 106 such as time of treatment, distance traveled, power output, current and cumulative, temperature, wavelength(s) in use, etc. Control unit 104 is connected to laser console 102 and treatment site 106 through connection fibers 108. Connection fiber 108 is connected to hand piece 112 which is the means to introduce optical fiber 110 into treatment site 106. Hand piece 112 includes a standard insertion needle at its distal end and has a hollow channel within its body for insertion of optical fiber. Hand piece 112 measures the speed of withdrawal of the optical fiber and relays the feedback to control unit 104 which then controls the power output from laser console 102. Laser console 102 would have two lasers of the appropriate wavelength incorporated therein and connected to control unit 104. Additionally, laser console 102 can house a motorized pull back device which can help uniformly withdraw the optical fiber 110 for use in certain treatments.

Figure 2:
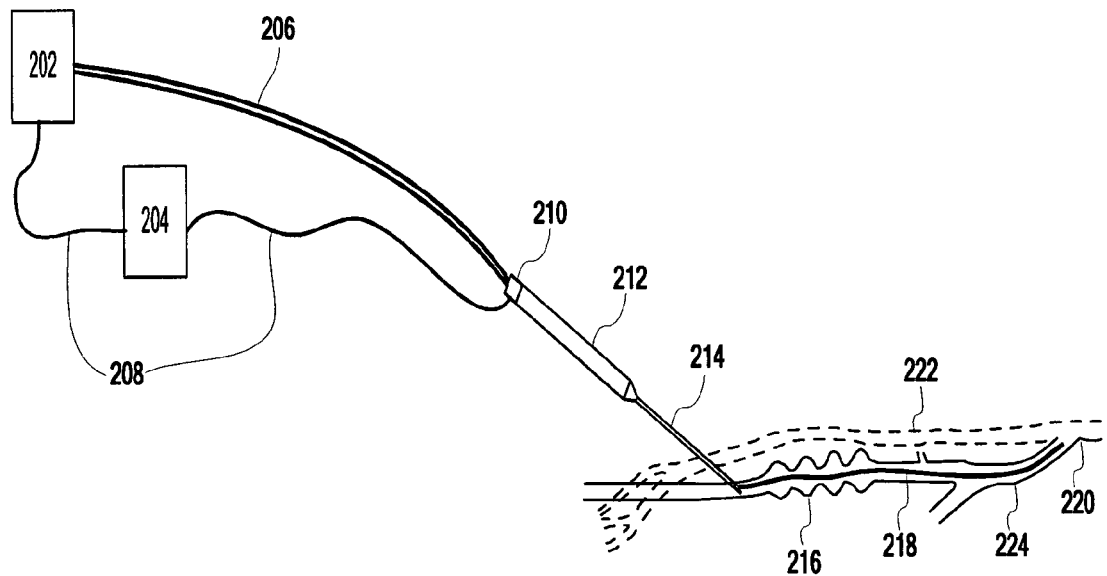
FIG. 2 shows the insertion of the fiber into the vein through the catheter with the fiber tip positioned at the saphenofemoral junction just prior to administration of energy.

FIG. 2 shows optical fiber 218 placed in the vein to be treated. In hand piece 212, needle 214 is positioned therein to be inserted into the vein to be treated. The vein to be treated is the Greater Saphenous Vein (GSV) 224, in this example, which joins Saphenous Vein 222 at Sapheno-Femoral joint 220. Optical fiber 218 is introduced into greater saphenous vein up to sapheno-femoral joint 220. Enlarged section 216 of GSV vein 224 is the region that might cause problems. Hand piece 212 has interface unit 210 to which laser console unit 202 is connected through fiber 206 and control unit 204 through link fibers 208. The information about the vein and treatment site is relayed to control unit 204 by interface unit 210 on hand piece 212. Control unit 204 based on the feedback directs power output to the vein through laser console 202. Optical fiber 218 passes from laser console 202 to sapheno-femoral junction 220 through connecting fiber 206, hand piece 212 and GSV 224.

Figure 3:
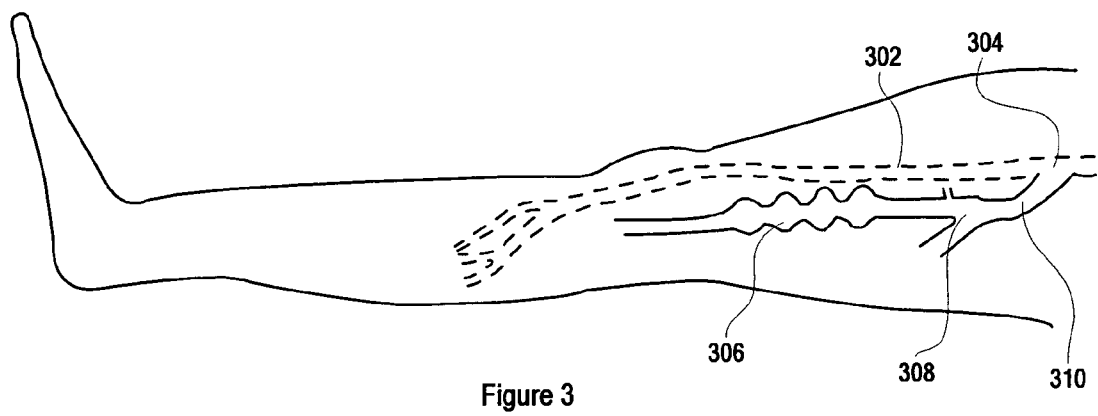
FIG. 3 is a representation of the varicose vein to be treated with feedback.

FIG. 3 is a depiction of varicose vein 306 to be treated. The abnormal varicose vein 306 is a part of Greater Saphenous Vein (GSV) 310, peripheral veins 308 bring blood from the extremities or body surface to the GSV. The GSV empties into saphenous vein 302 at sapheno-femoral junction 304.

Figure 4:
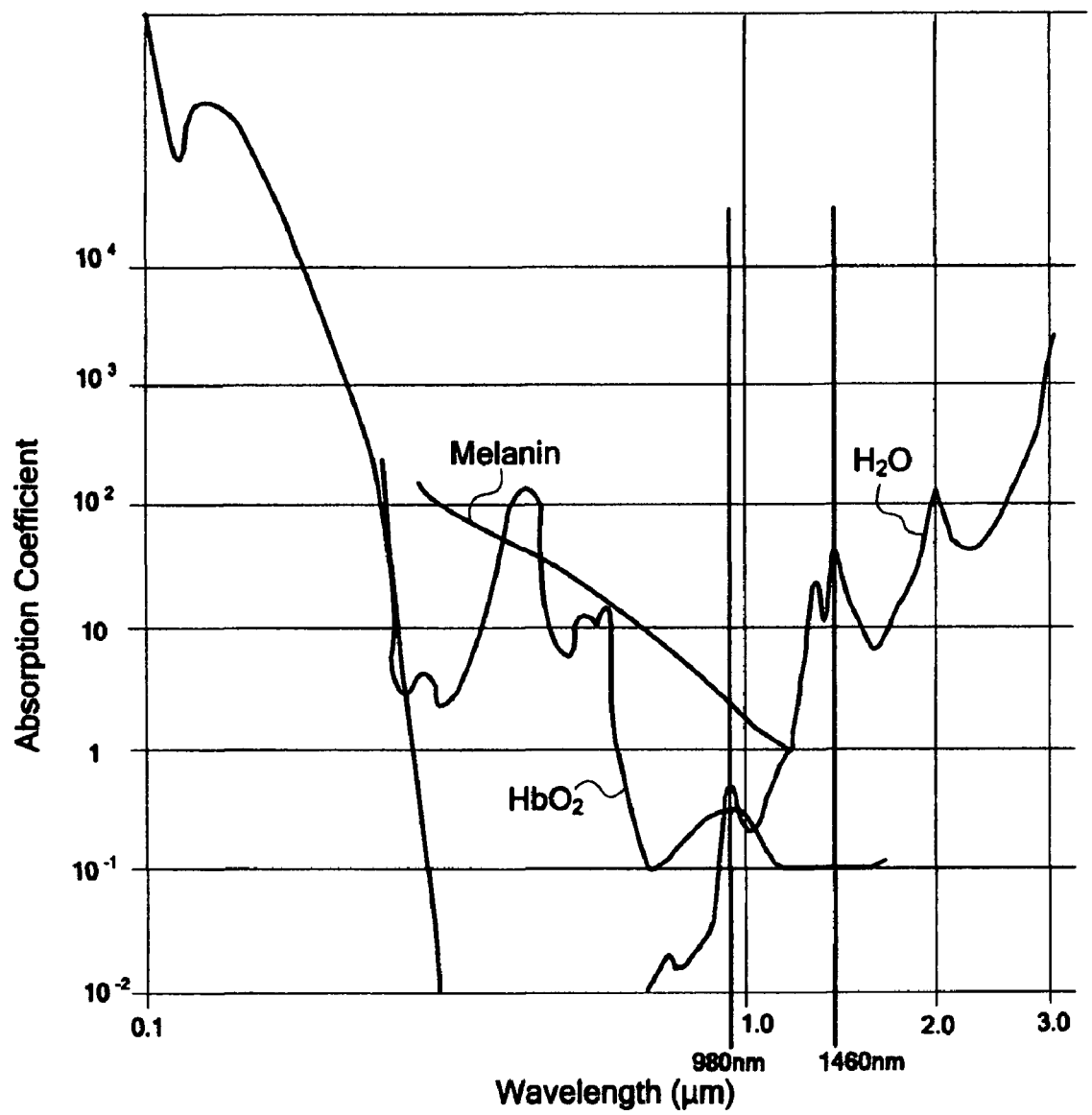
FIG. 4 shows the absorption curves of hemoglobin, oxyhemoglobin and water as a function of wavelength in the near infrared range.

FIG. 4 shows the graph of absorption coefficient of water, oxy-hemoglobin and melanin at different wavelengths. Absorption curve (θ σ curves in water & hemoglobin) indicates that the whole wavelength range is not equally useful (1.2-1.8 μm). The absorption curve of oxy-hemoglobin at 980 nm and the absorption curve of water at 1460 nm are shown. These wavelengths are an especially effective combination for the treatment of abnormal veins. The 980 nm wavelength is useful for absorption in blood: hemoglobin-water combination. The 1460 nm wavelength is useful for its higher absorption in water and collagen in the vein walls, and its much lower absorption in hemoglobin. The 1460 nm wavelength has about 20 times more water absorption capability than the 1320 nm wavelength and has about 50 times more water absorption capability than the 980 nm wavelength. Mixing possibility between two wavelengths is used to support or optimize the absorptions between blood and water, hence achieving the ideal penetration in respect to: age, size of vein, location of vein and proximity to nerve structures plus adding a direct irradiation of collagen-water in the vein walls. This combination combines technological enhancement with surgical benefits.

According to an exemplary embodiment, a laser vein treatment as according to FIG. 2, above, is administered to the GSV using a single 1460±60 nm wavelength. For example, in one embodiment, treatments are administered as a continuous wave at 1470 nm, with about a two minute to about a three minute pullback time. As described above, 1460±60 nm is useful for high absorption in water and collagen absorption in the vein walls. A single wavelength vein treatment at 1460±60 nm gives the added benefit of high vein closure rates combined with extremely favorable post-operative results. Namely, little, if any, post-operative pain/discomfort, brusing or inflammatory reactions are encountered, making 1460±60 nm treatments ideal for use in sensitive areas [such as legs or arms].

For many potential applications of an optical fiber for illumination/irradiation purposes, the limitation of the output angle is a great disadvantage. In order to irradiate/illuminate the desired area entirely, a diffuser tip is used. A diffuser tip is particularly useful in such applications in which it is desirable to heat, illuminate or to irradiate an object uniformly in order to obtain uniform, predictable and reproducible results. Diffusing tip fibers are known to be used with lasers to treat hyperproliferative tumors. Diffusing tip fibers in general require a scattering material at their tips in order to effectively diffuse the laser light to a treatment site. Use of diffusing tips could be useful for treatment of varicose veins as laser radiation can be directed perpendicularly from the diffuser tip to the treatment vein. This allows precise heating and destruction of the vein endothelial cells. Non-diffusing fiber tips direct the energy along the axis of the vein wherein uniform energy is not delivered to the vein walls. The use of a rounded diffusing tip will reduce the chances of perforating the vein with sharp edges.

Figure 5:
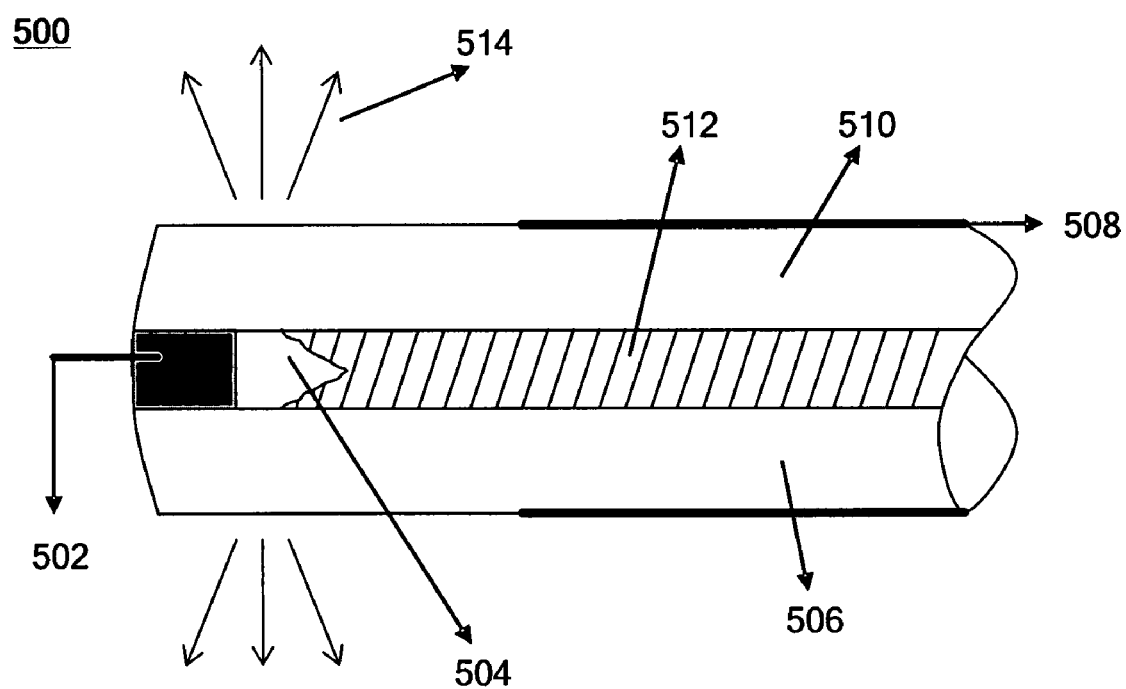
FIG. 5 is a representative view of a diffusing fiber tip.

FIG. 5 is a depiction of a special, side firing diffuser tip 500. This fiber substantially expands the definition commonly proposed for diffuser tips. Here a radially distributed beam is created to diminish forward firing and provide substantially radiation in all radial directions of the circumference of a vein wall. Optical fiber 506 has inner core 512 and outer cladding 510; the optical fiber has plastic coating 508 on the outer surface. The diffuser tip has quartz block 502 fused into the core opening of the optical fiber. The diffuser tip has a portion of the core removed to form an air/void gap 504 and the fiber core end is shaped to form a V-notched end. Air/void gap 504 between V-notched core end and fused quartz block acts as a diffusing means for the laser light. The void in the core is created by a micro machining technique to form the conical gap. This void is then closed with a quartz block fused into the gap to form a diffuser tip. The laser radiation pattern 514 is emitted perpendicular to the vein walls which gives the shortest way from the fiber tip to the vein walls.

In an alternative embodiment, the diffuser tip 500 may, in fact, represent a lasing medium 512 that not only radiates in the axial direction but radiates radially from the tip 500. Using more common diffuser tips where the laser energy is scattered radially towards the vein wall over an extended length of fiber tip also works within the scope of this invention. In particular for extended section inner wall treatment at modest power levels and extended diffusing section permits longer exposure time of specific wall sections as the fiber tip is being pulled back towards its entry point. The length of the diffusing section, its output together with information on the vein size, can be used to determine proper pull back speed to properly irradiate the interior wall requiring treatment.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claim.

What is claimed:

1. An underskin laser treatment system for the treatment of skin irregularities, elimination of vascular abnormalities and general assistance in surgical procedures comprising:
   a hand piece fitted with a catheter or needle, said hand piece having a hollow channel within its body and having a proximal end and a distal end;
   a radiation source emitting two different wavelengths of radiation, one wavelength being absorbed primarily by hemoglobin-water and the other wavelength being absorbed primarily by water-collagen in a wall of a vein to effect closure of said vein;
   wherein said radiation source is a laser source emitting radiation of about 980±20 nanometers and about 1460±60 nanometers; and
   an optical fiber, said optical fiber connected to said radiation source and passing through said hand piece and said catheter or needle.

2. The underskin laser treatment system according to claim 1, wherein the radiation source simultaneously emits and adjusts radiation of said first wavelength and radiation of said second wavelength to maximize the effects of each wavelength during treatment.

3. The underskin laser treatment system according to claim 1, wherein said optical fiber includes a diffuser section on said distal end.

4. The underskin laser treatment system according to claim 3, wherein said diffuser section includes a tip having a cone-notched end of a fiber core, an air gap, a block, said air gap being between said cone-notched end and said block.

5. The underskin laser treatment system according to claim 1 further including a control unit for monitoring and controlling operating parameters including laser output power, pulsed or continuous laser operation, pull back speed of said optical fiber, time of operation, said control unit connected to said radiation source and to an interface device on said hand piece by a separate optical fiber.

6. The underskin laser treatment system according to claim 1, further including a motorized pull back device for translating said optical fiber in said vein.

7. A method for underskin laser treatment of skin irregularities, vascular abnormalities and general assistance in surgical procedures comprising the steps of:
    identifying a vein or other area for treatment;
    using a catheter or needle to position an optical fiber with an output tip in said vein or other area selected for treatment; and
    irradiating said vein as said optical fiber is withdrawn, said irradiating comprising radiation of two wavelengths of radiation, a first wavelength being absorbed by primarily hemoglobin-water and a second wavelength being absorbed by primarily water-collagen in a wall of said vein to effect the closure of veins
    wherein said two wavelengths are about 980±20 nanometers and about 1460±60 nanometers.

8. The method for underskin laser treatments of skin irregularities or vascular abnormalities and general assistance in surgical procedures according to claim 7, wherein said irradiating is controlled based on operating parameters including radiation power, time, distance, and withdrawal speed of said optical fiber.

9. The method for underskin laser treatments according to claim 7, characterized in that for treatment of inner body structures, said optical fiber is guided into said vein or other area for treatment by imaging devices to insure positioning of a distal tip of said optical fiber.

10. The method for underskin laser treatments according to claim 7, characterized in that said irradiating is from a fiber tip emitting radiation radially in a full circumferential manner perpendicular to the axis of said tip.

11. The method for underskin laser treatments according to claim 7, characterized in that the radiation of first wavelength and radiation of the second wavelength are simultaneously input and adjusted accordingly to maximize the effects of each wavelength during treatment.

12. The method for underskin laser treatments according to claim 7, characterized in that said optical fiber is withdrawn from said vein with a motorized pull back device.

13. The method for underskin laser treatments according to claim 7, characterized in that said first wavelength of said radiation is provided in a pulsed mode and is absorbed by primarily hemoglobin-water to seal said vein, and said second wavelength of said radiation is absorbed by primarily water-collagen in said wall of said vein to effect the closure of said vein.

* * * * *